(12) United States Patent
Reimann et al.

(10) Patent No.: US 11,756,691 B2
(45) Date of Patent: Sep. 12, 2023

(54) BRAIN HEALTH COMPARISON SYSTEM

(71) Applicants: Martin Reimann, Tucson, AZ (US); Oliver Schilke, Tucson, AZ (US)

(72) Inventors: Martin Reimann, Tucson, AZ (US); Oliver Schilke, Tucson, AZ (US)

(73) Assignees: Martin Reimann, Tucson, AZ (US); Oliver Schilke, Tucson, AZ (US)

( * ) Notice: Subject to any disclaimer, the term of this patent is extended or adjusted under 35 U.S.C. 154(b) by 663 days.

(21) Appl. No.: 16/241,967

(22) Filed: Jan. 7, 2019

(65) Prior Publication Data

US 2020/0043615 A1   Feb. 6, 2020

Related U.S. Application Data

(60) Provisional application No. 62/713,260, filed on Aug. 1, 2018.

(51) Int. Cl.
*G16H 50/70* (2018.01)
*G16H 50/30* (2018.01)
(Continued)

(52) U.S. Cl.
CPC .............. *G16H 50/70* (2018.01); *A61B 5/055* (2013.01); *A61B 5/4064* (2013.01); *G16H 50/20* (2018.01);
(Continued)

(58) Field of Classification Search
CPC ........ G16H 50/70; G16H 50/30; G16H 50/20; G16H 10/60; A61B 5/055; A61B 5/4064; A61B 5/4088
(Continued)

(56) References Cited

U.S. PATENT DOCUMENTS 5,927,988 A   7/1999   Jenkins
6,159,014 A   12/2000  Jenkins
(Continued)

FOREIGN PATENT DOCUMENTS

CN   104851101 A   8/2015
CN   104866727 A   8/2015
(Continued)

OTHER PUBLICATIONS

Reimann, M., Schilke, O., Weber, B., Neuhaus, C., & Zaichkowsky, J. (2011). Functional magnetic resonance imaging in consumer research: A review and application. Psychology & Marketing, 28(6), 608-637. (Year: 2011).*

(Continued)

*Primary Examiner* — Joshua B Blanchette
*Assistant Examiner* — Winston Furtado

(57) ABSTRACT

Systems and methods for determining a predicted brain health of a first user and providing individualized health recommendations to the first user based at least in part on an artificial neural network trained on previously existing anatomical and functional neuroimaging information, behavioral information, self-reported information, and other types of information of a plurality of users. The artificial neural network may be capable of determining a predicted benchmark of brain health of the first user's information when compared with the previously existing users' information and storing the first user's anatomical and/or functional neuroimaging information, behavioral information, self-reported information, and other types of information in a database such that the artificial neural network can be re-trained based on the new information of the first user. The first user can be notified of his or her brain health and receive individualized health recommendations.

11 Claims, 17 Drawing Sheets

(51) Int. Cl.
    *A61B 5/055*     (2006.01)
    *G16H 50/20*     (2018.01)
    *A61B 5/00*     (2006.01)
    *G16H 10/60*     (2018.01)

(52) U.S. Cl.
    CPC ............ *G16H 50/30* (2018.01); *A61B 5/4088* (2013.01); *G16H 10/60* (2018.01)

(58) Field of Classification Search
    USPC .......................................................... 705/2
    See application file for complete search history.

(56) References Cited

U.S. PATENT DOCUMENTS

| | | |
|---|---|---|
| 6,261,101 B1 | 7/2001 | Benitz |
| 6,280,198 B1 | 8/2001 | Calhoun |
| 6,463,315 B1 | 10/2002 | Klinberg |
| 6,565,359 B2 | 5/2003 | Calhoun |
| 6,629,844 B1 | 10/2003 | Jenkins |
| 7,317,821 B2 | 1/2008 | Chen |
| 7,647,098 B2 | 1/2010 | Prichep |
| 7,961,922 B2 | 6/2011 | Spence |
| 7,986,991 B2 | 7/2011 | Prichep |
| 8,209,224 B2 | 6/2012 | Pradeep |
| 8,270,814 B2 | 9/2012 | Pradeep |
| 8,386,312 B2 | 2/2013 | Pradeep |
| 8,392,250 B2 | 3/2013 | Pradeep |
| 8,392,255 B2 | 3/2013 | Pradeep |
| 8,464,288 B2 | 6/2013 | Pradeep |
| 8,484,081 B2 | 7/2013 | Pradeep |
| 8,494,905 B2 | 7/2013 | Pradeep |
| 8,655,437 B2 | 2/2014 | Pradeep |
| 8,977,110 B2 | 3/2015 | Pradeep |
| 9,332,954 B2 | 5/2016 | Vestevich |
| 9,357,941 B2 | 6/2016 | Simon |
| 9,420,970 B2 | 8/2016 | Dagum |
| 9,474,481 B2 | 10/2016 | Dagum |
| 9,519,981 B2 | 12/2016 | Sudarsky |
| 9,538,948 B2 | 1/2017 | Dagum |
| 9,633,430 B2 | 4/2017 | Fan |
| 9,687,187 B2 | 6/2017 | Dagum |
| 9,693,724 B2 | 7/2017 | Dagum |
| 9,886,981 B2 | 2/2018 | Pradeep |
| 9,993,190 B2 | 6/2018 | Preminger |
| 10,140,628 B2 | 11/2018 | Pradeep |
| 2004/0092809 A1 | 5/2004 | DeCharms |
| 2006/0112050 A1* | 5/2006 | Miikkulainen ........ G16H 50/20 706/46 |
| 2007/0166675 A1 | 7/2007 | Atkins |
| 2007/0191704 A1 | 8/2007 | DeCharms |
| 2009/0025023 A1 | 1/2009 | Pradeep |
| 2009/0267945 A1 | 10/2009 | Warntjes |
| 2009/0318794 A1 | 12/2009 | DeCharms |
| 2010/0145215 A1 | 6/2010 | Pradeep |
| 2010/0249538 A1 | 9/2010 | Pradeep |
| 2010/0250325 A1 | 9/2010 | Pradeep |
| 2011/0046504 A1 | 2/2011 | Pradeep |
| 2011/0106750 A1 | 5/2011 | Pradeep |
| 2011/0237971 A1 | 9/2011 | Pradeep |
| 2012/0330109 A1* | 12/2012 | Tran ....................... A61B 5/681 600/301 |
| 2013/0185144 A1 | 7/2013 | Pradeep |
| 2013/0245424 A1 | 9/2013 | DeCharms |
| 2014/0316248 A1 | 10/2014 | DeCharms |
| 2015/0018630 A1 | 1/2015 | Fotuhi |
| 2016/0015289 A1 | 1/2016 | Simon |
| 2016/0081575 A1 | 3/2016 | Wu |
| 2017/0053540 A1 | 2/2017 | Meagher |
| 2017/0086698 A1 | 3/2017 | Wu |
| 2017/0087301 A1 | 3/2017 | Wu |
| 2017/0109881 A1 | 4/2017 | Avendi |
| 2017/0112392 A1 | 4/2017 | Wu |
| 2017/0112407 A1 | 4/2017 | Wu |
| 2017/0258382 A1 | 9/2017 | Dagum |
| 2017/0258383 A1 | 9/2017 | Dagum |
| 2017/0323485 A1 | 11/2017 | Samec |
| 2018/0137941 A1 | 5/2018 | Chen |
| 2018/0315188 A1 | 11/2018 | Tegzes |

FOREIGN PATENT DOCUMENTS

| | | |
|---|---|---|
| CN | 105796097 A | 7/2016 |
| CN | 106250707 A | 12/2016 |
| EP | 2709061 A1 | 3/2014 |
| WO | 2000044283 A1 | 8/2000 |
| WO | 2010147913 A1 | 12/2010 |
| WO | 2018005814 A1 | 1/2018 |

OTHER PUBLICATIONS

Ashburner, J., Barnes, G., Chen, C., Daunizeau, J., Flandin, G., Friston, K., . . . & Penny, W. (2015). SPM12 manual. Welcome Trust Centre for Neuroimaging, London, UK, 2464. (Year: 2015).*
Ventola, C. L. (2014). Social media and health care professionals: benefits, risks, and best practices. Pharmacy and therapeutics, 39(7), 491. (Year: 2014).*
Liu, J., Pan, Y., Li, M., Chen, Z., Tang, L., Lu, C., & Wang, J. (2018). Applications of deep learning to MRI images: A survey. Big Data Mining and Analytics, 1(1), 1-18. (Year: 2018).*
Bengio, Learning Deep Architectures for AI, Foundations and Trends in Machine Learning, 2009, 1-127, 2(1), Now Publishers Inc., Hanover, MA, USA.
Nathawani, Neuroscience Meets Deep Learning, 2016.
Chen, From "Where" to "What": Distributed Representations of Brand Associations in the Human Brain, Journal of Marketing Research, 2015, 453-466, 51(4), Berkeley, CA, USA.
Wu, Introduction to Convolutional Neural Networks, National Key Lab for Novel Software Technology, 2017, Nanjing University, CN.
Glorot, Deep Sparse Rectifier Neural Networks, Proceedings of the 14th International Conference on Artificial Intelligence and Statistics (AISTATS), 2011, 15, Ft. Lauderdale, FL, USA.
Just, A Neurosemantic Theory of Concrete Noun Representation Based on the Underlying Brain Codes, PLOS One, 2010, 5(1), Pittsburgh, PA, USA.
Just, Machine Learning of Neural Representations of Suicide and Emotion Concepts Identifies Suicidal Youth, Nature Human Behaviour, 2017, 911-919, 1.
Kim, Deep Neural Network with Weight Sparsity Control and Pre-Training Extracts Hierarchical Features and Enhances Classification Performance: Evidence from Whole-Brain Resting-State Functional Connectivity Patterns of Schizophrenia, NeuroImage, 2016, 127-146, 124.
Krizhevsky, ImageNet Classification with Deep Convolutional Neural Networks, Communications of the ACM, Jun. 2017, 84-90, 60(6), New York, NY, USA.
Greff, LSTM: A Search Space Odyssey, Transactions on Neural Networks and Learning Systems, Oct. 2017, 2222-2232, 28(10).
Hochreiter, Long Short-Term Memory, Neural Computation, 1997, 1735-1780, 9(8).
Liu, Visual Listening In: Extracting Brand Image Portrayed on Social Media, 2018, 1-50.
Mandal, Structural Brain Atlases: Design, Rationale, and Applications in Normal and Pathological Cohorts, J. Alzheimers Dis. 2012, S169-S188, 31(03).
Mitchell, Predicting Human Brain Activity Associated with the Meanings of Nouns, Science, 2008, 1191-1195, 320 (5880).
Neelakantan, Neural Programmer: Inducing Latent Programs With Gradient Descent, ICLR 2016, 1-18.
Norman, Beyond Mind-Reading: Multi-Voxel Pattern Analysis of fMRI Data, Trends in Cognitive Sciences, 2006, 424-430, 10(9).
Pascanu, On the Difficulty of Training Recurrent Neural Networks, Proceedings of the 30th International Conference on Machine Learning, JMLR:W&CP, 2013, 1-9, 28.
Scholz, Training Induces Changes in White Matter Architecture, Nat. Neurosci., 2009, 1370-1371, 12(11).

(56) References Cited

OTHER PUBLICATIONS

Vieira, Using Deep Learning to Investigate the Neuroimaging Correlates of Psychiatric and Neurological Disorders: Methods and Applications, Neuroscience and Biobehavioral Reviews, 2017, 58-75, 74.
Yamins, Using Goal-Driven Deep Learning Models to Understand Sensory Cortex, Nature Neuroscience, 2016, 356-365, 19(3).
Weber, A Domain-specific Risk-attitude Scale: iVleasuring Risk Perceptions and Risk Behaviors, Journal of Behavioral Decision Making, 2002, 263-290, 15.
Sherif, CBRAIN: A Web-Based, Distributed Computing Platform for Collaborative Neuroimaging Research, Frontiers in Integrative Neuroscience, 2014, 1-13, 8(54).
Sherif, BrainBrowser: Distributed, Web-Based Neurological Data Visualization, 2015, Frontiers in Neuroinformatics, 1-10, 8(89).
Josef, Stability and Change in Risk-Taking Propensity Across the Adult Lifespan, Journal of Personality and Social Psychology, 2015, 430-450, 111(3).

\* cited by examiner user jane doe

. your working memory

. stronger than 75% of peers
. predicts financial success 85% of times
. predicts happiness 10% of times
. predicts dementia 5% of times . to learn more about this brain area,
  consider these publications . to strengthen this brain area,
  consider these recommendations . schedule next brain scan in 22 days

FIG. 10F personalized recommendations

Before receiving suggestions on how to improve your brain health, we ask that you complete the following assessment of your personal health-risk propensity. this will allow for calibrating the intensity of suggested recommendations.

For each of the following statements, please indicate the likelihood of engaging in each activity. provide a rating from 1 to 5, using the scale below:

|  | extremely unlikely |  |  | extremely likely |  |
|---|---|---|---|---|---|
| Eating 'expired' food products that still 'look okay'. | 1 | 2 | 3 | 4 | 5 |
| Frequent binge drinking. | 1 | 2 | 3 | 4 | 5 |
| Ignoring persistent physical pain by not going to the doctor. | 1 | 2 | 3 | 4 | 5 |
| Taking a medical drug that has negative side effects. | 1 | 2 | 3 | 4 | 5 |
| Never using sunscreen when you sunbathe. | 1 | 2 | 3 | 4 | 5 |
| Never wearing a seatbelt. | 1 | 2 | 3 | 4 | 5 |
| Not having a smoke alarm in or outside of your bedroom. | 1 | 2 | 3 | 4 | 5 |
| Smoking a pack of cigarettes per day. | 1 | 2 | 3 | 4 | 5 |

FIG. 10G

BRAIN HEALTH COMPARISON SYSTEM

CROSS-REFERENCE TO RELATED APPLICATIONS

This application claims priority to and benefit of provisional application No. 62/713,260, filed on Aug. 1, 2018, the entire contents of which are incorporated by reference herein.

BACKGROUND OF THE INVENTION

Field of the Invention

The present invention relates to the field of human health. More specifically, the present invention relates to providing individualized health reports and recommendations.

Background of the Invention

As early as one's 20's, one's cognitive ability and brain health begin to progressively decline, with millions of people diagnosed with brain-based productivity problems and cognitive declines each year. Often, declines in cognitive function are detected after clinical symptoms have manifested and substantial deterioration has occurred and may be irreversible. Opportunities to obtain information about brain health are limited to clinical or research settings, but the former requires a diagnosis and/or symptoms of cognitive decline that have already taken effect, while the latter strives for generalization and extrapolation from small sample sizes to the general population and is not aimed at providing individualized brain health information for particular individuals. Moreover, there is no comprehensive system or database for storing different types of brain data and non-brain data together (e.g., anatomical, functional, behavioral, survey self-reports, genetic etc.), comparing an individual's brain data against the stored data, and providing information and individualized recommendations related to the individual's brain health before any clinical symptoms of cognitive decline have manifested.

There is a need for methods and systems for providing individuals with their brain health information and tailored brain health reports and recommendations without a clinical diagnosis, medical necessity for doing so, or participation in research studies that are not directed to the individual. There is a further need for methods and systems for storing multiple types of brain data, including anatomical, functional, behavioral, survey, genetic, and other types of brain data in a database, assaying an individual's brain data against the stored brain data, providing individualized brain health information and recommendations, and, with consent, making the information available to the individual and to various audiences.

BRIEF SUMMARY OF THE INVENTION

The present invention seeks to deliver a solution to these problems by providing a comprehensive brain health comparison system that allows for analyzing brain information, including through the various types of data discussed above; visualizing brain structure and activation; predicting health outcomes using computational deep-learning techniques; comparing behavioral and neurophysiological performance to other users; and developing customized recommendations for possible treatments. Preferably, users can access the brain health comparison system through a graphical user interface accessed online or through remote devices such as a mobile phone or tablet. The interface is preferably extremely intuitive for the user to navigate a visual representation of brain structure and function and obtain customized information on brain health and associated recommendations in non-clinical and non-traditional research settings.

In these respects, the brain health comparison system of the present invention substantially departs from the conventional concepts and designs of the prior art. Its computerized, automated design affords more accurate and less time-consuming diagnosis of brain health at an individual level, preferably along with an easy-to-navigate multi-dimensional visualization that facilitates a user's exploration of the brain. Further, the brain health comparison system preferably leverages large samples in order to identify particular brain regions associated with relevant health outcomes, and, among other methods, makes use of functional magnetic resonance imaging (fMRI) that has high spatial resolution and offers both structural and functional information. Preferably, the brain health comparison system is also able to integrate a variety of other types of data that help to jointly assess brain health as well as relevant antecedents, mechanisms, and outcomes, including behavioral data, genetic data, and other self-report data. Finally, the brain health comparison system is preferably designed such that it allows not only physicians, clinicians, and scientists but also patients, relatives of patients, caregivers, and other end users to obtain access to their data through a user interface.

While the systems and methods discussed herein are described in connection with assessment of the human brain and human brain health, the systems and methods are not limited to use in connection with the human brain and may be implemented to assess health of any human body organ and/or health outcome. The systems and methods set forth below are not limited to the specific embodiments described herein. In addition, components of each system and steps of each method can be practiced independently and separately from other components and method steps described herein. Each component and method step also can be used in combination with other systems and methods.

BRIEF DESCRIPTION OF THE DRAWINGS

The present invention will now be more particularly described, with reference to the accompanying drawings, by way of example only and in no way limiting the scope of the invention, in which:

FIGS. 10A-10H illustrate user interface examples.

DETAILED DESCRIPTION

The present invention can be implemented in many ways, including as a process; an apparatus; a system; a non-transitory computer readable program product embodied on a computer readable storage medium; and/or a processor, such as a processor configured to execute instructions on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term processor refers to one or more devices, circuits, and/or processing cores configured to process information, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example only and the invention may be practiced according to the claims without some or all of these specific details. For the purpose of clarity, technical material that is known in the technical fields related to the invention has not been described in detail.

Figure 1:
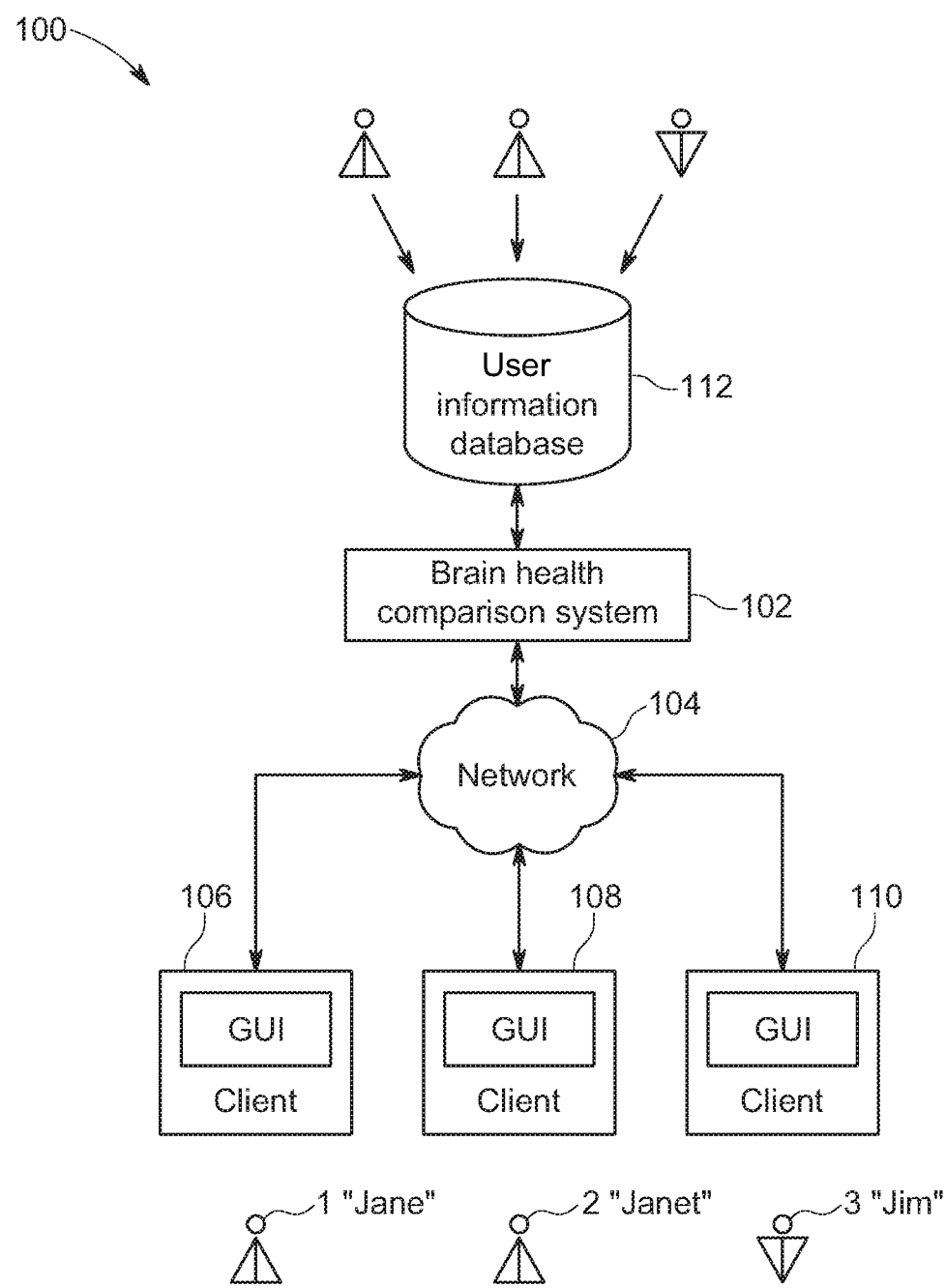
FIG. 1 is a high-level flowchart illustrating an embodiment of a health prediction system.

FIG. 1 is a high-level flowchart illustrating an embodiment of a health prediction system 100 configured in accordance with the present invention and is not intended to limit scope as one of ordinary skill in the art would understand on review of this application that other configurations could be utilized without departing from the scope of the claimed invention. In this embodiment, system 100 is implemented in connection with assessment of the human brain. In this embodiment, system 100 includes brain health comparison system 102, which may be implemented using one or more server computers having one or more processors, one or more special purpose computing appliances, or any other appropriate hardware, software, or combinations thereof capable of implementing and/or executing computer readable instructions. The operations of the brain health comparison system 102 are described in greater detail below.

In this embodiment, various users of the system (e.g., user 1 "Jane", user 2 "Janet", and user 3 "Jim") access the brain health comparison system via a network 104 using client devices 106, 108, 110. In one embodiment, network 104 may be a cloud-based storage and processing system. Alternatively, network 104 may be a network of server computers, connected to store and process information. Client devices 106, 108, 110 may be a computer, a mobile phone or device, a tablet, or any other such device that allows a user to access network 104. Database 112 stores user information, including functional neuroimaging information; anatomical neuroimaging information; behavioral information, which may be acquired during neuroimaging scan sessions; self-reported information; other behavioral information such as but not limited to information from users' stationary and mobile devices such as smartphones and smartwatches, other wearable devices such as fitness armbands etc.; and health-monitoring information etc. pertaining to the users. Database 112 can be implemented on an integral storage component of the brain health comparison system, an attached storage device, a separate storage device accessible by the brain health comparison system, or combinations thereof.

Many different arrangements of the physical components of the brain health comparison system are possible in various embodiments. In various embodiments, the entirety of the collected anatomical and functional neuroimaging information is stored in a database 112 to facilitate the brain health comparison system 102. For example, in preferred embodiments, voxels are extracted from the brain images of participants undergoing anatomical and/or functional neuroimaging scans, such as fMRI, and assayed and stored in database 112. Because the human brain varies in size among individuals, the number of voxels extracted, assayed, and stored may range in number, depending on the size of the brain undergoing a neuroimaging scan. Based on the average size of the human brain, preferably approximately 700,000 1-millimeter gray-matter, cortical voxels may be extracted in an anatomical neuroimaging scan and approximately 26,000 3-millimeter isotropic functional voxels may be extracted in a functional neuroimaging scan, and then assayed and stored in database 112. However, the numbers of voxels extracted, assayed, and stored by the present invention are not limited to these quantities, and one of skill in the art would understand the present invention may extract, assay, and store a greater or smaller quantity of voxels depending on the size of the brain being undergoing assessment.

Figure 2:
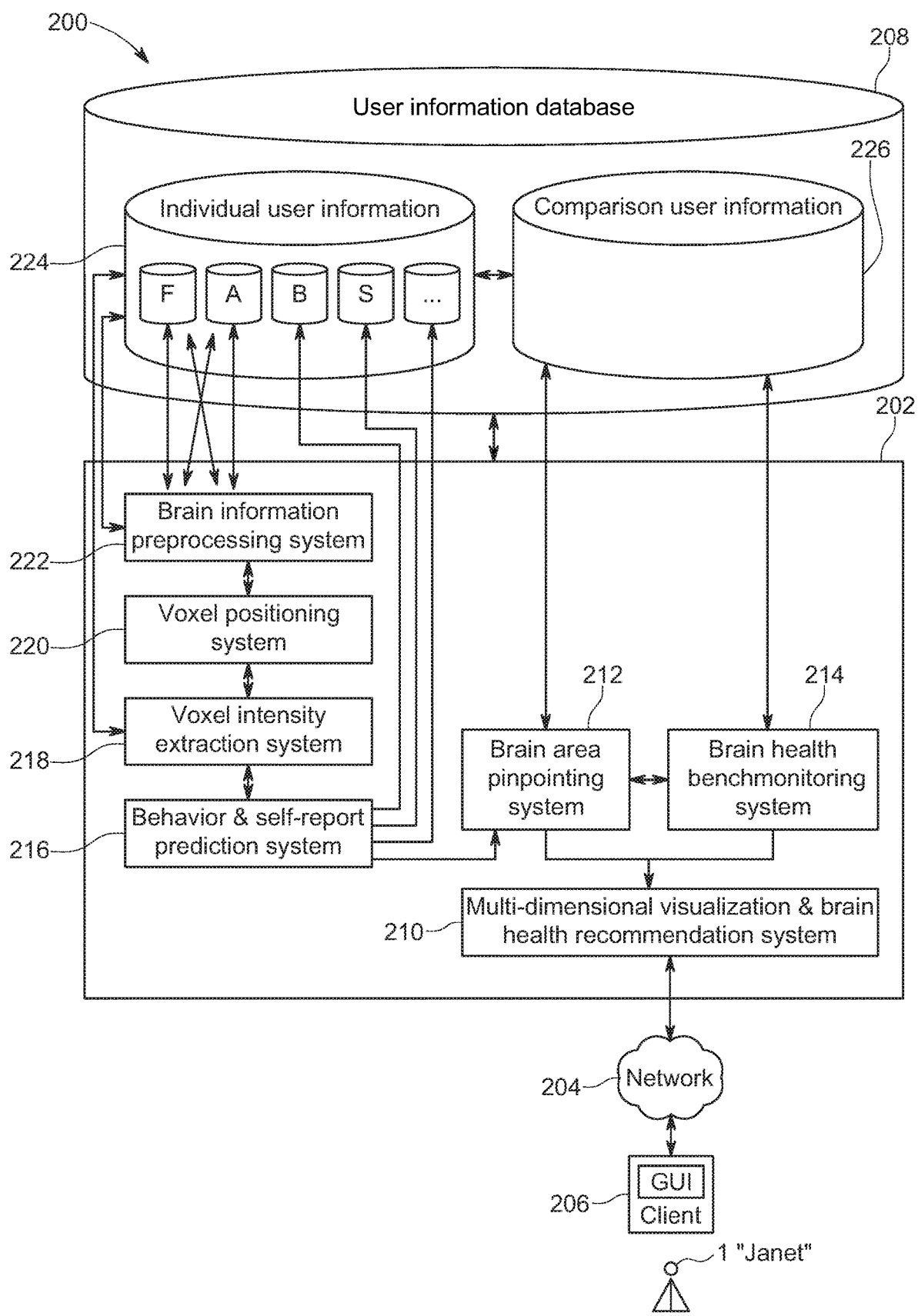
FIG. 2 is a detailed flowchart illustrating an embodiment of a health prediction system.

FIG. 2 is a detailed flowchart illustrating an embodiment of a health prediction system 200 configured in accordance with the present invention and is not intended to limit scope as one of ordinary skill in the art would understand on review of this application that other configurations could be utilized without departing from the scope of the claimed invention. In this embodiment, system 200 is implemented in connection with assessment of the human brain. In this embodiment, system 200 includes brain health comparison system 202, which may be implemented using one or more server computers having one or more processors, one or more special purpose computing appliances, or any other appropriate hardware, software, or combinations thereof capable of executing computer readable instructions. In this embodiment, data may be exchanged between pieces of software and/or different servers, storage memory, systems, and/or components. In this embodiment, user 1 ("Jane") accesses the brain health comparison system 202 of system 200 via a network 204 using client devices such as 206, as described with respect to FIG. 1. Both individual user information 224 (e.g., user 1 "Janet") and comparison user information 226 are stored in a database 208. Database 208 stores individual user information 224, which may include functional neuroimaging information F and anatomical neuroimaging information A taken from brain scans of individuals, through, for example, fMRI. Individual user information 224 stored in database 208 also contains behavioral information B taken during scan sessions (e.g., numerical behavioral responses) and self-reported information S taken from individuals' self-reports. Database 208 may also store other behavioral information such as information on users' stationary and mobile devices as well as health monitoring information etc., denoted " . . . " in database 208. Data F, A, B, S, and " . . . " are stored in individual information system 224 within user information database 208. The frontend of the brain health comparison system 202 is a multi-dimensional visualization and brain health recommendation system 210, described in greater detail at FIG. 9 below, in which users can view multi-dimensional visualizations of their brain information, access statistics and reports, and share information with other users.

Database 208 receives information from a brain area pinpointing system 212 (described in greater detail at FIG. 8 below) and a brain health benchmarking system 214 (described in greater detail at FIG. 8 below), using comparison user information 226 in a database 208. The brain area pinpointing system 212 and brain health benchmarking system 214 compare the performance of specific brain areas in user e.g., user 1 "Janet" in FIG. 2 to the performance of the specific brain areas of other users. Brain area pinpointing system 212 and brain health benchmarking system 214 receive information from a behavior and self-report prediction system 216. Behavior and self-report prediction system 216 integrates behavioral and self-report data, and uses neuroimaging information from voxel extraction system 218. Voxel extraction system 218 extracts a numerical brain activation value from each voxel. Upon receiving information from voxel extraction system 218, behavior and self-report prediction system 216 predicts user information as described in greater detail at FIG. 7, including behavioral information acquired during neuroimaging scan sessions (denoted "B" in 208), self-reported information (denoted "S" in 208), and other information denoted " . . . " in 208. Voxel positioning system 220 (described in greater detail at FIG. 5 below) enables voxel intensity extraction system 218 (described in greater detail at FIG. 6 below) to define a brain activation value for any given voxel identified by a x-y-z coordinate across time in multi-dimensional space. Voxel positioning system 220 receives information from a brain information preprocessing system 222 (described in greater detail at FIG. 4 below). Brain information preprocessing system 222 receives information from individual user information 224 in database 208, which contains functional neuroimaging information (denoted "F" in system 208) and anatomical neuroimaging information (denoted "A" in system 208). While the preferred embodiment is described above for illustrative purposes, the invention is not limited to such an embodiment and other configurations of the invention are contemplated as would be understood by one skilled in the art.

Figure 3:
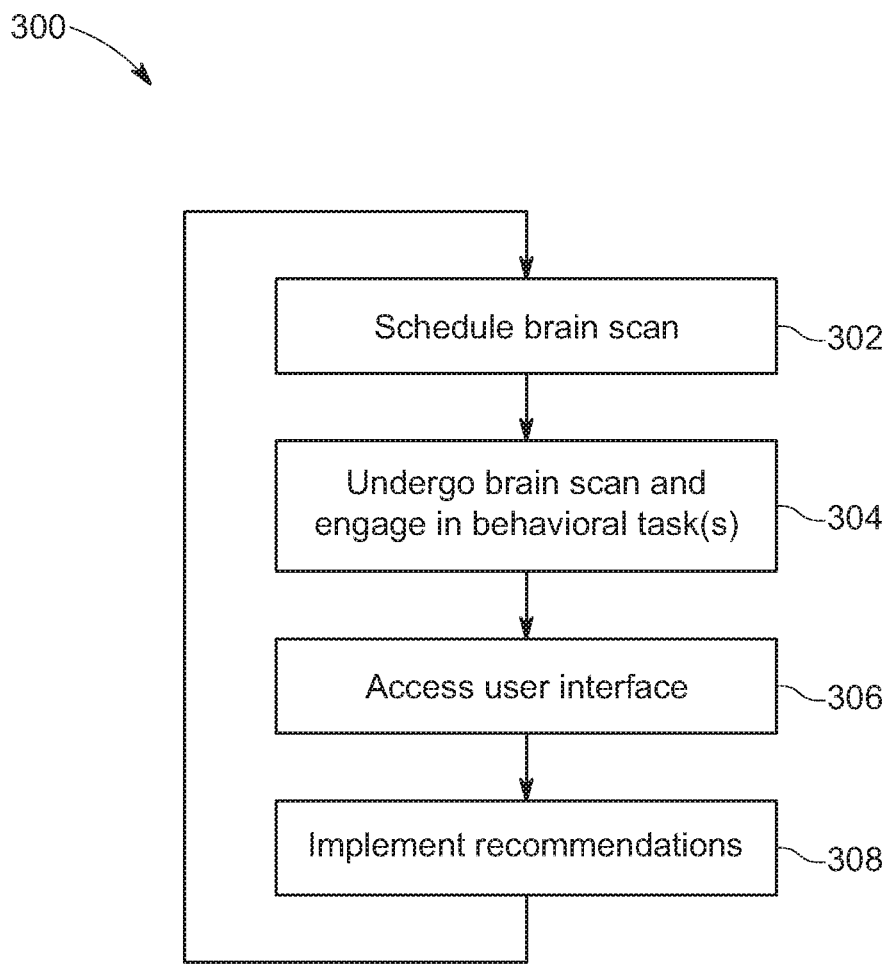
FIG. 3 is a flowchart illustrating an embodiment of a user experiential process of a health prediction system.

FIG. 3 is a flowchart illustrating an embodiment of a user experiential process 300 in accordance with the present invention and is not intended to limit scope as one of ordinary skill in the art would understand on review of this application that other arrangements could be utilized without departing from the scope of the claimed invention. Experiential process 300 may be implemented on a health prediction system such as system 100 or system 200. Many different arrangements of the steps of a user experiential process 300 are possible in various embodiments. In this embodiment, at 302, a user begins the user experiential process by making a reservation for a neuroimaging brain scan. User may make a reservation by using an electronic device (e.g., a personal computer, a mobile device or phone, a tablet) to access an online scheduling system, by making a reservation by phone, in person, or through other communication channels. During the scheduling process 302, user responds to prescreening questions in order to determine eligibility for brain scanning. For example, prescreening questions may include medical history, current medications, and/or metal in or on one's body (e.g., pacemakers, tattoos).

At 304, a user undergoes a brain scan, for example, at an imaging facility. Brain scans may be conducted by use of, though not limited to, fMRI machines, such as those manufactured by Siemens (e.g., Magnetom, Biograph, Mobile MRI Scanner), Philips (e.g., Achieva, Ingenia), General Electrics (e.g., Signa), and other manufacturers. Such brain scans may involve a user engaging in certain tasks that allow for collection of functional, anatomical, behavioral, and/or self-reported information. During the brain scan 304, a user may be engaged in one or multiple behavioral tasks while the user's anatomical and/or functional neuroimaging information is collected. Each behavioral task represents standardized, structured, and precisely timed presentations of stimulus material and user prompts to respond to the stimulus material, for example, perception of abstract geometrical shapes presented in different colors, or perception of and interaction with concrete symbols such as playing cards and scenarios involving monetary gains and losses as indications of risk-prone or risk-averse behaviors. Stimulus materials may be presented through over-head projections or viewing goggles while the user is positioned within the brain scanner as would be understood in the art. Behavioral responses may be collected through button-box or other collection devices, which allow users to provide behavioral responses on a multi-button response box held in the user's hand. Behavioral tasks may assess cognitive function, including impulse control, self-control, attentional control, working memory, memory span, long-term memory, autobiographical memory, intelligence, verbal, auditory, and visual processing, selection of appropriate options, risk-taking, gambling, card sorting, and/or other cognitive abilities, though this list is neither exhaustive nor exclusive and the present invention is not limited to such behavioral tasks or cognitive assessments. Upon completion of the brain scan, or at any other point during the user experiential process 300, a user may respond to several survey questions, for example, pertaining to a user's overall health and lifestyle choices.

At 306, a user logs in to a brain health comparison system's user interface, such as depicted at 206 in system 200, via e.g., a personal computing and viewing device such as a desktop computer, laptop computer, tablet computer, and/or mobile phone. Other devices that provide access to a network via a user interface are also contemplated by the invention. Once a user logs into brain health comparison system's interface 306, user will be able to browse through visualizations of user's brain; obtain prediction and comparison reports; obtain suggestions on scholarly publications relevant to certain brain conditions; obtain referrals to specialists that are directed toward certain aspects of a user's brain and/or brain function; receive opportunities for information sharing with other people; and receive personalized brain health recommendations (as seen at FIGS. 10A-10H). Exemplary recommendations may include interventions such as physical activities, cognitive exercises, changes in lifestyle or habits, and/or dietary suggestions, etc. Other recommendations for maximizing brain health are contemplated within the scope of the invention. At 308, a user may consider implementing some of the recommendations obtained by accessing user interface during 306. A user may schedule another brain scan 302, for example, to target another brain function and/or monitor changes over time.

Figure 4:
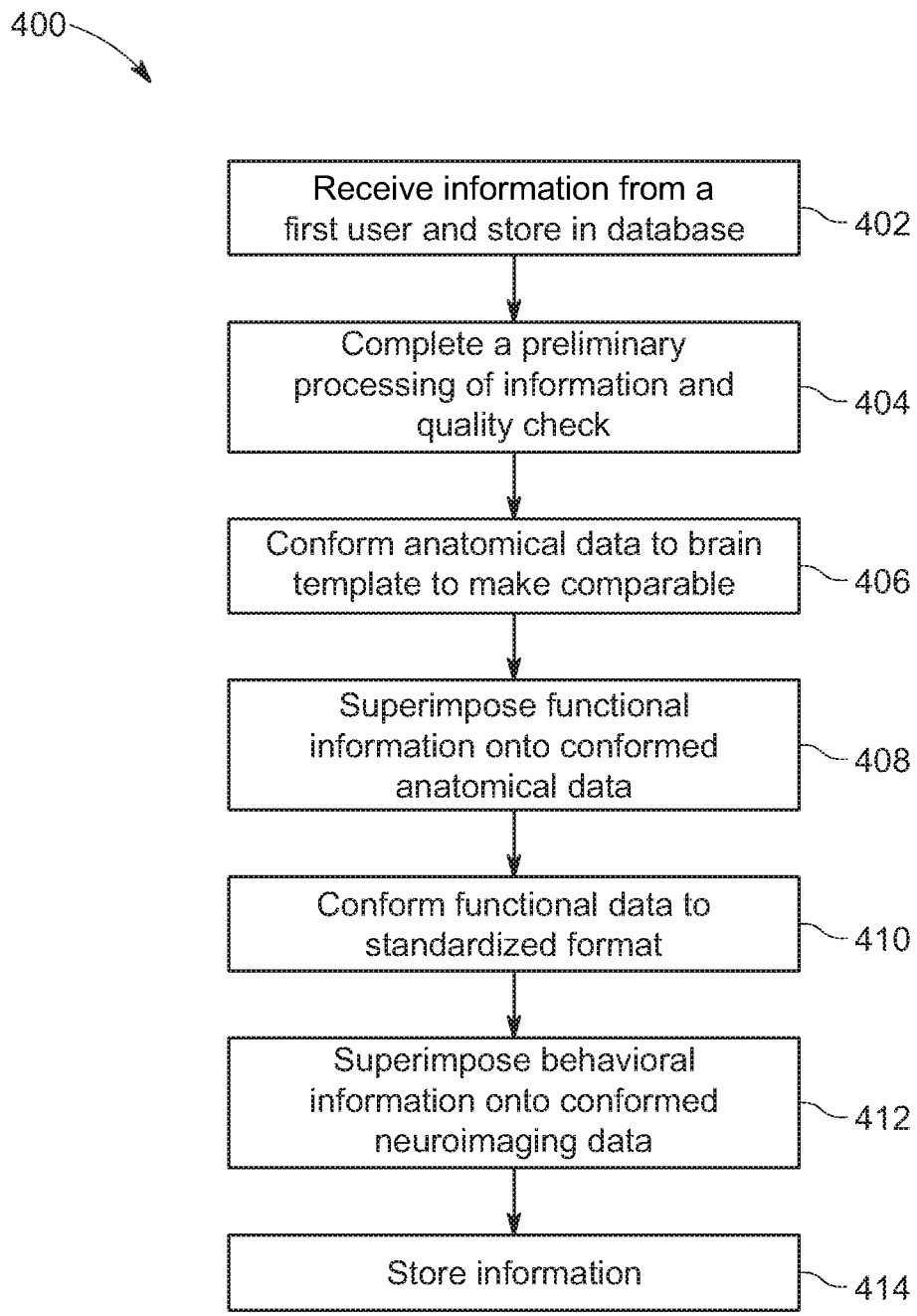
FIG. 4 is a flowchart illustrating an embodiment of a brain information preprocessing process.

FIG. 4 is a flowchart illustrating an embodiment of a brain information preprocessing process 400 in accordance with the present invention and is not intended to limit scope as one of ordinary skill in the art would understand on review of this application that other arrangements could be utilized without departing from the scope of the claimed invention. Brain information preprocessing process 400 may be implemented by brain information preprocessing system 222 in system 200. Many different arrangements of the steps of a brain information preprocessing process, and the components of a brain information preprocessing process system, are possible in various embodiments. In this embodiment, at 402, information of a first user is received from a neuroimaging scanner (such as fMRI), the behavioral response collection devices, and self-report surveys, and stored in a database, such as 208, as described above with respect to FIG. 2. User information may include raw functional neuroimaging information, raw anatomical neuroimaging information, behavioral information acquired during neuroimaging scan sessions, and self-reported information. At 404, preliminary processing of raw functional neuroimaging information and raw anatomical neuroimaging information is undertaken, neuroimaging information quality is checked, and behavioral and self-reported information is organized.

Preliminary processing of the neuroimaging information may include slice-scan-timing correction, temporal high pass filtering, three-dimensional motion correction, inhomogeneity correction, ISO matrix transformation, spatial normalization and alignment, brain tissue segmentation, and surface reconstruction as is known in the art. At 406, the anatomical neuroimaging information is conformed to a standardized brain template (e.g., preferably 1-millimeter cortical voxels but which could range from 1 micrometer to 3 centimeters in size) in order to make information comparable to other users. A voxel positioning system, as described with respect to FIG. 5, facilitates this step. At 406, an image of the skull and other matter (e.g., fat, skin, and tissue) is also removed computationally to allow a direct view of the brain. At 408, the functional neuroimaging information is superimposed onto the conformed anatomical neuroimaging information in order to match each functional information point (e.g., regions of detected brain activity) with its corresponding anatomical information point. At 410, functional neuroimaging information is conformed to a standardized format. Said standardized format may preferably be 3-millimeter isotropic functional voxels, though the format can range from micrometers to centimeters in size. At 412, the behavioral information is superimposed onto the conformed functional and anatomical neuroimaging information in order to match each time point of a behavioral task to the corresponding neuroimaging information points. At 414, a final dataset is stored in a database such as 208.

Figure 5:
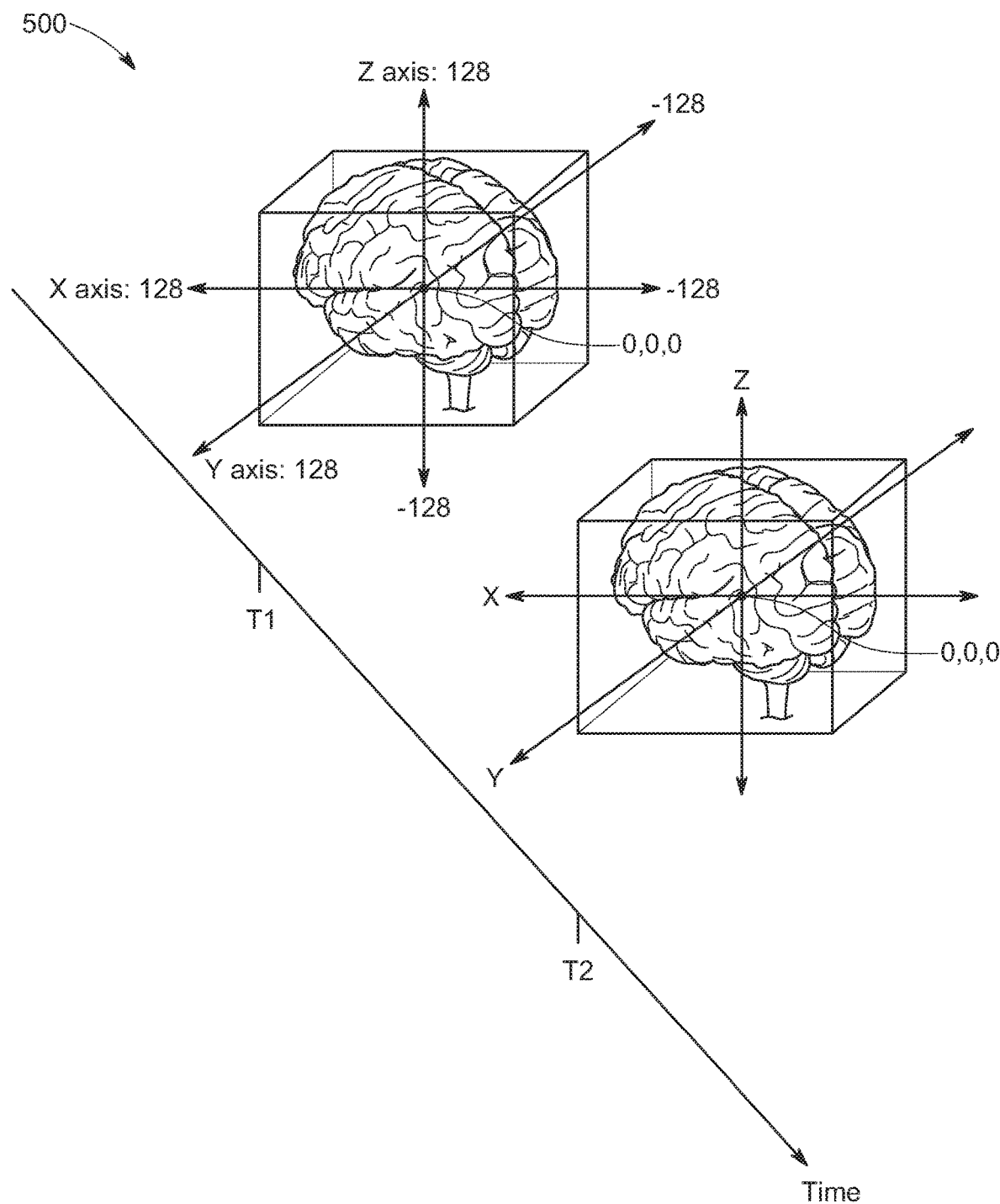
FIG. 5 is a multi-dimensional view illustrating an embodiment of a voxel positioning system.

FIG. 5 is a multi-dimensional view illustrating an embodiment of a voxel positioning system 500 such as 220 in system 200 configured in accordance with the present invention and is not intended to limit scope as one of ordinary skill in the art would understand on review of this application that other configurations could be utilized without departing from the scope of the claimed invention. Many different arrangements of the steps of a voxel positioning process, and the components of a voxel positioning system, are possible in various embodiments. In this embodiment, neuroimaging information is collected over time and spaced in a matrix, which may preferably be a matrix comprising 256 points× 256 points×256 points, but the present invention is not limited to such dimensions and other three-dimensional configurations (e.g., 128×128×128) are also contemplated within the scope of the invention. Each data point may reflect the raw blood oxygenation value at each coordinate corresponding to a region of the brain for each time point (e.g., T1, T2, T3, etc.) for each brain. The raw blood oxygenation may then be normalized to a value between 0 and 1 to account for any differences in baseline blood oxygenation levels between users. For example, the normalized blood oxygenation value may preferably be computed as follows: (open raw blood oxygenation values−mean blood oxygenation values)/standard deviation. However, the present invention is not limited to any particular method of normalizing such values. In this embodiment, at time point T1, 16,777,216 data points (=256×256×256) are collected and each data point is assigned its own x-y-z coordinate. For example, the coordinate at the very center of the box is x: 0, y: 0, z: 0. Voxel positioning is repeated at time points T2, T3, T4, and so on until the end of the behavioral task. The preferable resolution of the described analyses is by example only and may be either higher or lower in other embodiments.

Figure 6:
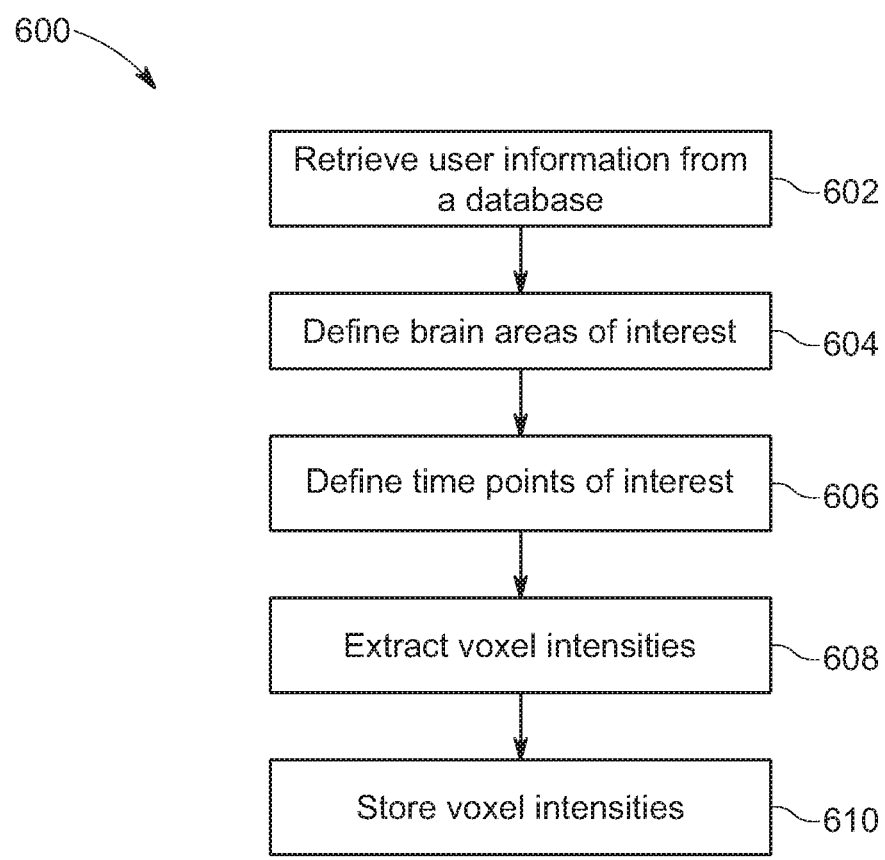
FIG. 6 is a flowchart illustrating an embodiment of a voxel intensity extraction process.

FIG. 6 is a flowchart illustrating an embodiment of a voxel intensity extraction process 600 in accordance with the present invention and is not intended to limit scope as one of ordinary skill in the art would understand on review of this application that other arrangements could be utilized without departing from the scope of the claimed invention. Process 600 may be implemented in connection with voxel intensity extraction system 218 in system 200. Many different arrangements of the steps of a voxel intensity extraction process, and the components of a voxel intensity extraction system, are possible in various embodiments. In this embodiment, at 602, stored information from voxel positioning system 500 is retrieved from a database, such as 208. At 604, brain areas of interest are defined (e.g., in cubic form), containing voxels with specific x-y-z coordinates as described in voxel extraction system 500 at FIG. 5. At 606, time points of interest are defined, for example, in a millisecond time span, ranging from 10,000 ms to 14,000 ms in some embodiments. For example, time points of interest may present phases before, during, and/or after a user has responded to a stimulus, has made a decision, has provided a button press or performed any other activity while undergoing a brain scan. At 608, voxel intensities (i.e., the brain activation values in a specific brain area at a specific time point) are extracted. When used in conjunction with fMRI, voxel intensities may reflect levels of blood oxygenation at specific brain areas as indicative of the relative levels of activation at each brain area at a given point in time. At 610, voxel intensities are stored in a database. Voxel intensities may be stored in a tabular format.

Figure 7:
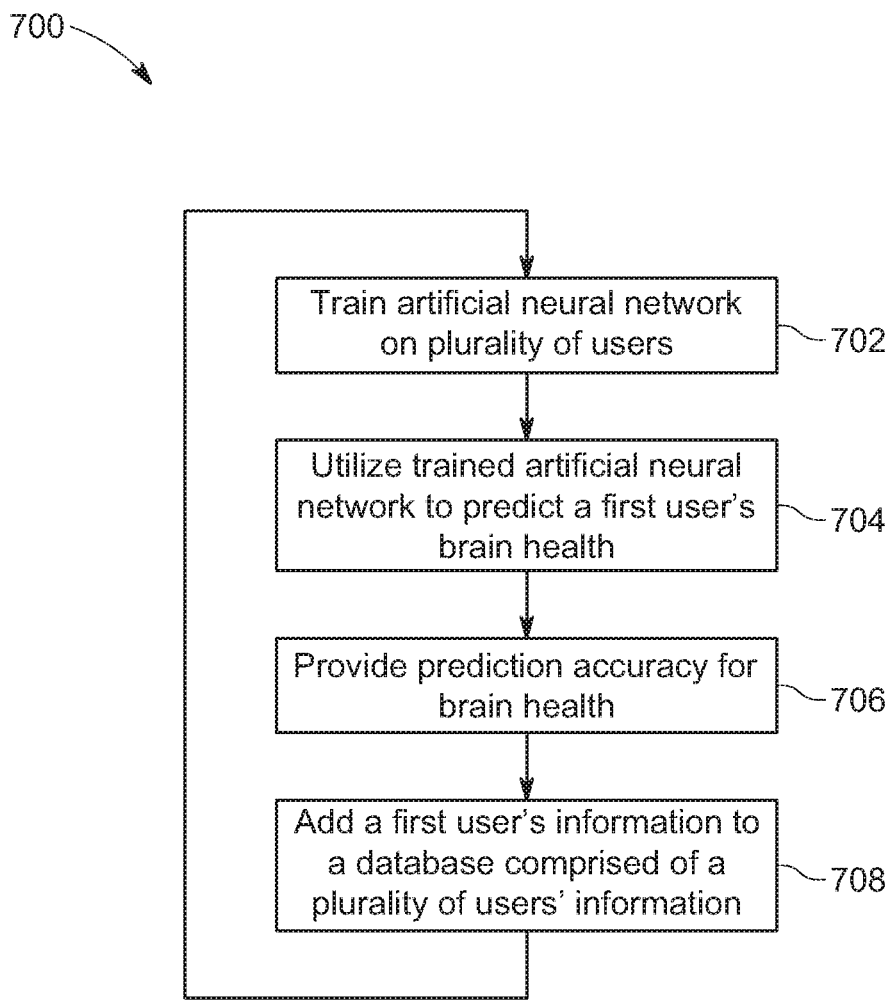
FIG. 7 is a flowchart illustrating an embodiment of a behavior and self-report prediction process.

FIG. 7 is a flowchart illustrating an embodiment of a behavior and self-report prediction process in accordance with the present invention and is not intended to limit scope as one of ordinary skill in the art would understand on review of this application that other arrangements could be utilized without departing from the scope of the claimed invention. Behavior and self-report prediction process 700 may be implemented by behavior and self-report prediction system 216 in system 200. Many different arrangements of the steps of a behavior and self-report prediction process, and the components of a behavior and self-report prediction system, are possible in various embodiments. In this embodiment, at 702, an artificial neural network is trained on previously existing user information. The artificial neural network may be a convolutional neural network and/or a recurrent neural network (e.g., long short-term memory neural network), as is understood in the art, though the present invention is not limited to such networks. Previously existing user information may comprise functional, anatomical, behavioral, self-report, genetic, and other data obtained from users as described above. An artificial neural network extracts information such as voxel intensities (as described at 600 in FIG. 6) or behavioral and self-reported information (as described under system 200 in FIG. 2) from users stored in a database such as 208 to recognize patterns in the voxel intensities and predict behavioral and self-reported information based on recognized patterns in the functional neuro-imaging information. For example, an artificial neural network classifies voxel intensities to provide a likelihood of a user making a particular decision on a behavioral task or responding in a certain way to a stimulus (e.g., "85% risky choice" or "90% working memory"). At 704, a first user's information (e.g., user 1 "Janet") is added to previously existing user information and the artificial neural network predicts brain health based on neuroimaging information. For example, user 1's behavioral information is added to the previously existing user information. An artificial neural network trained on previous user information is then fed user 1's voxel intensities as described at 600 in FIG. 6. At 706, a behavior and self-report prediction system provides a prediction accuracy. For example, user 1's voxel intensities of a region of user 1's brain (e.g., prefrontal cortex) predict with high likelihood a particular behavioral decision, based on a plurality of previous user information stored in database such as 208. At 708, user 1's information is added to the database of previously existing user information and an artificial neural network is trained again, now with the added information obtained from user 1.

Figure 8:
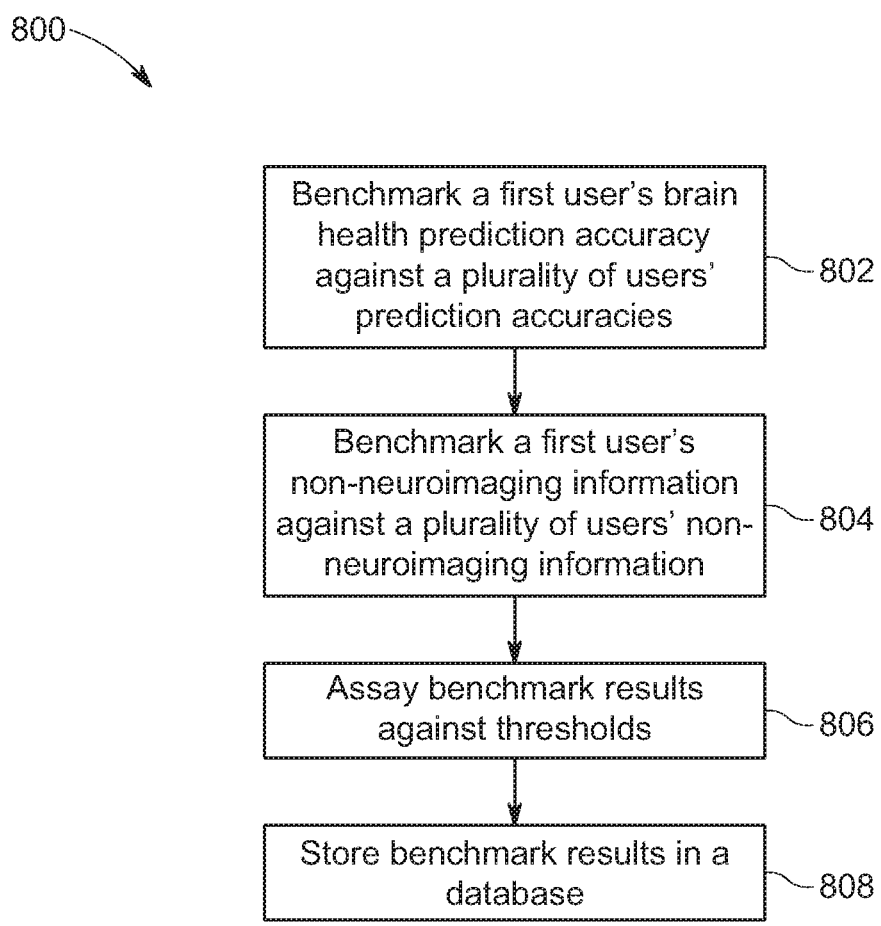
FIG. 8 is a flowchart illustrating an embodiment of a brain area pinpointing process and a brain health benchmarking process.

FIG. 8 is a flowchart illustrating an embodiment of a brain area pinpointing process 800 in accordance with the present invention and is not intended to limit scope as one of ordinary skill in the art would understand on review of this application that other configurations could be utilized without departing from the scope of the claimed invention. Brain area pinpointing process 800 may be implemented by brain area pinpointing system 212 and brain health benchmarking system 214 in system 200. Many different arrangements of the steps of a behavior and self-report prediction process, and the components of a behavior and self-report prediction system, are possible in various embodiments. In this embodiment, at 802, a user's prediction accuracy (as described at 706 in FIG. 7) for a specific brain area and a specific behavioral task is benchmarked against previously existing user information in a database. For example, user 3's prediction accuracy is assayed and compared against prediction accuracies (e.g., expressed in a measure-of-central-tendency such as mean, median, mode etc.) of all user information in a database or a specific subset of users in a database (e.g., selected by age, sex, gender, ethnicity, education, occupation etc.). At 804, a user's non-neuroimaging information (e.g., behavioral information, self-reported information etc.) is assayed and compared against non-neuroimaging information (e.g., expressed in a measure-of-central-tendency such as mean, median, mode etc.) of all user information in a database or a specific subset of users in a database. At 806, benchmarking results of 802 and 804 are assayed against thresholds to determine abnormalities, malfunctions, deviations, and other irregularities in the prediction accuracy of a user, their behavioral performances, their self-reported responses, and combinations thereof. For example, the comparison thresholds preferably include quartiles (e.g. "different than upper quartiles" or "different than fourth quartile") and percentages (e.g., "different than 80% of users" or "different than 90% of users"). At 808, results of this comparison and threshold examination are stored in a database such as 208 for example.

Figure 9:
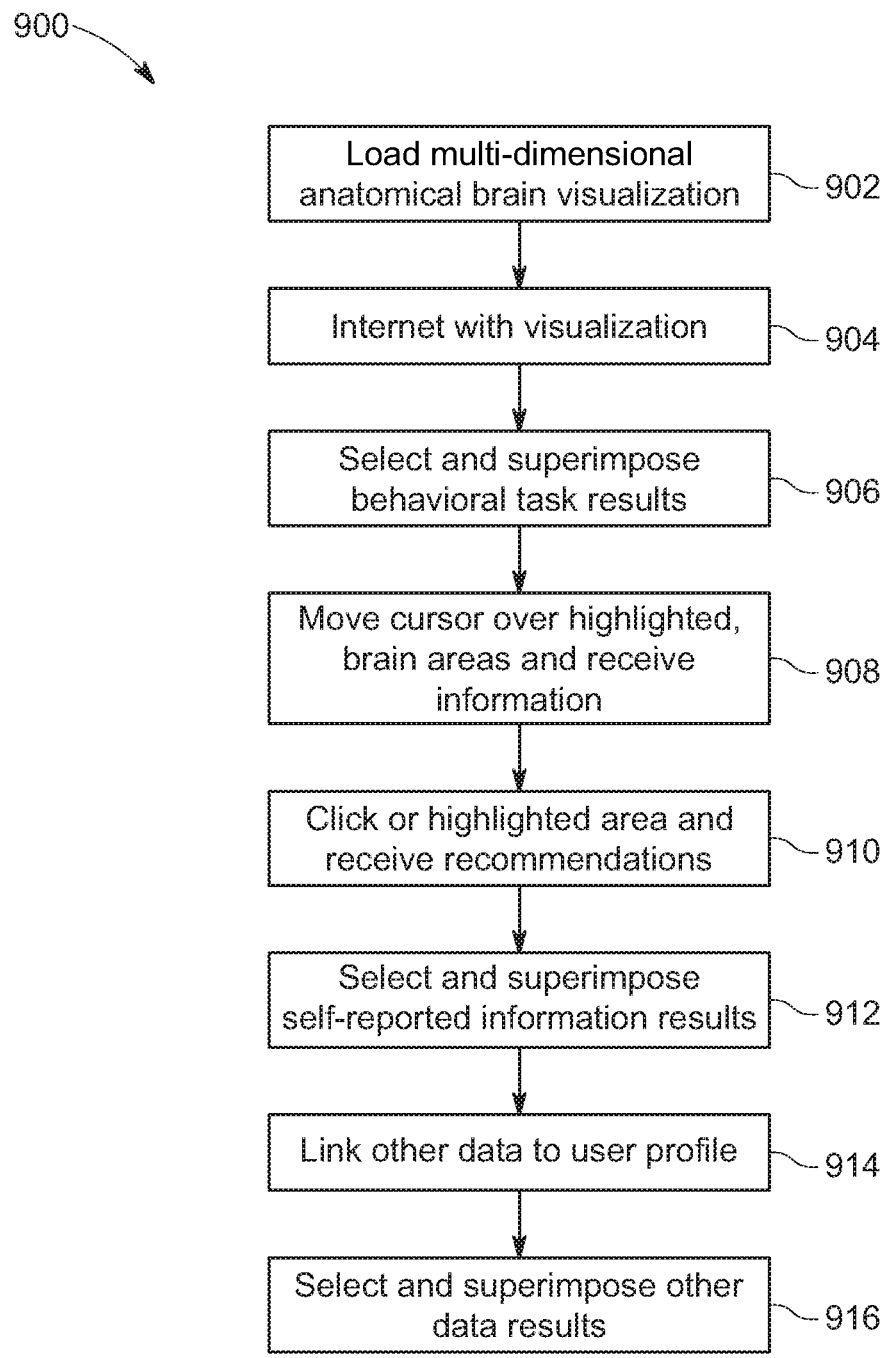
FIG. 9 is a flowchart illustrating an embodiment of a multi-dimensional visualization and brain health recommendation process.

FIG. 9 is a flowchart illustrating an embodiment of a multi-dimensional visualization and brain health recommendation process 900 in accordance with the present invention and is not intended to limit scope as one of ordinary skill in the art would understand on review of this application that other arrangements could be utilized without departing from the scope of the claimed invention. Multi-dimensional visualization and brain health recommendation process 900 may be implemented by multi-dimensional visualization and brain health recommendation system 210 in system 200. Many different arrangements of the steps of a multi-dimensional visualization and brain health recommendation process, and the components of a multi-dimensional visualization and brain health recommendation system, are possible in various embodiments. In this embodiment, at 902, a multi-dimensional anatomical brain visualization (e.g., three-dimensional view or four-dimensional view including three space dimensions and one time dimension) is loaded in an Internet browser and/or a mobile application, or other personal viewing device. At 904, a user interacts with the anatomical brain visualization. A user may interact with the anatomical brain visualization, for example, by using pan/zoom controls, slider/toggle controls, and light/shade controls to vary the angle/tilt of the brain and the degree of brain slice segmentation in order to expose the brain's deeper layers in horizontal, sagittal, and coronal slices. The present invention is not limited to the above forms of interaction with the anatomical brain visualization, and other forms of interaction with the anatomical brain visualization are contemplated as would be understood in the art. At 906, a user selects a behavioral task that the user engaged with during a neuroimaging scan session. Several available tasks may be shown. Some tasks may be active if the user participated in them, while other tasks may be inactive if the user has not yet participated in them. The functional neuroimaging information corresponding to the selected behavioral task is then loaded and superimposed on the multi-dimensional anatomical brain visualization. The anatomical visualization now shows functional brain activation in certain brain areas, corresponding to specific phases of the selected behavioral task. Preferably, warm colors such as yellow and red may be used to indicate varying degrees of brain activation at specific phases of each selected task. However, the present invention is not limited to such colors and any indications of brain activation may be used. For example, in a gambling task, a user may select between "choice of a safe gamble" phase and "choice of a risky gamble" phase to see which of their brain areas predicted safe versus risky gambling behavior.

At 908, a user moves a cursor over the highlighted brain areas and, after doing so, receives statistical and textual information on the selected brain area. The information may include, but is not limited to, performance statistics on the behavioral task (e.g., "80% choice of risky gambles and 20% choice of safe gambles"), prediction statistics of the brain area (e.g., "prefrontal cortex predicts safe choice 65% of the time"), and comparison statistics (e.g., "the prefrontal cortex of other users in the same age group predicts safe choice 95% of the time"). However, the present invention is not limited to such examples.

At 910, a user clicks on or highlights the brain area of interest to receive personal brain health recommendations. These recommendations may include, for example, personalized health risk analyses, such as reports on potential risks related to the health of the prefrontal cortex; potential risks related to compulsive gambling; potential risks related to incurring excessive debt; potential risks related to cognitive decline across the life span; potential risks related to the interplay between mild cognitive impairment and/or dementia and risky decision making. Additional recommendations are contemplated by brain recommendation system and the invention is not limited to the exemplary recommendations. As part of the health risk analyses, brain recommendation system may provide links to scientific reports published in peer-reviewed scholarly journals in academic fields such as neuroscience, medicine, psychology, psychiatry, genetics, health management, well-being, public health, and/or economics relevant to the brain area clicked on or highlighted by the user, or relevant to other non-anatomical (e.g., behavioral) information provided by user. Brain health recommendations may also include well-being analyses, such as customized recommendations for strengthening the selected brain area. For example, recommendations may include interventions pertaining to physical activities, cognitive exercises, changes in habits, dietary suggestions, directed toward certain aspects of a user's brain and/or brain function. As part of the well-being analyses, links to scientific reports may be provided, as previously discussed, and users may receive referrals to specialists in the user's geographic area. Specialists may include neurologists, psychologists, and physicians. Users may also receive connections to and be provided with sharing options with other users that show similar sociodemographic characteristics and/or similar and/or related results. For example, users may choose to connect to other users in the same age group, the same geographical location, and/or the same sex/gender etc. Further, users may connect to other users that have similar anatomical, functional, and/or behavioral results.

At 912, a user selects a segment of self-reported information provided by the user, for example, sociodemographic information, phenotypes such as personality traits and other individual differences, well-being, happiness, satisfaction with life, risk-taking, financial decision making. For each of these segments, health risk and well-being analyses are provided, as discussed under 905. At 914, a user may link other data forms to his or her profile. For example, a user may optionally link his or her profile to data such as health monitoring information tracked by the user's smart watch or fitness armband (e.g., how much the user moves, how many steps the user takes, nutritional information), credit card information (e.g., outstanding balances, balance overdue, number of accounts open), genotype information (e.g., profiles from DNA decoding services), and/or social media information (e.g., number of social connections). At 916, a user selects a segment of other information he or she had linked to his or her profile. For each of these segments, health risk and well-being analyses are provided, as discussed at 905. These analyses are based on correlations, regressions, and other statistical methods in conjunction with the extant neuroimaging, behavioral, and self-report information. For example, a user's self-reported health risk data is correlated with his or her brain activation and a correlation coefficient is displayed to the user such as "Your health risk is 80% correlated with activation in your prefrontal cortex."

Figure 10A:
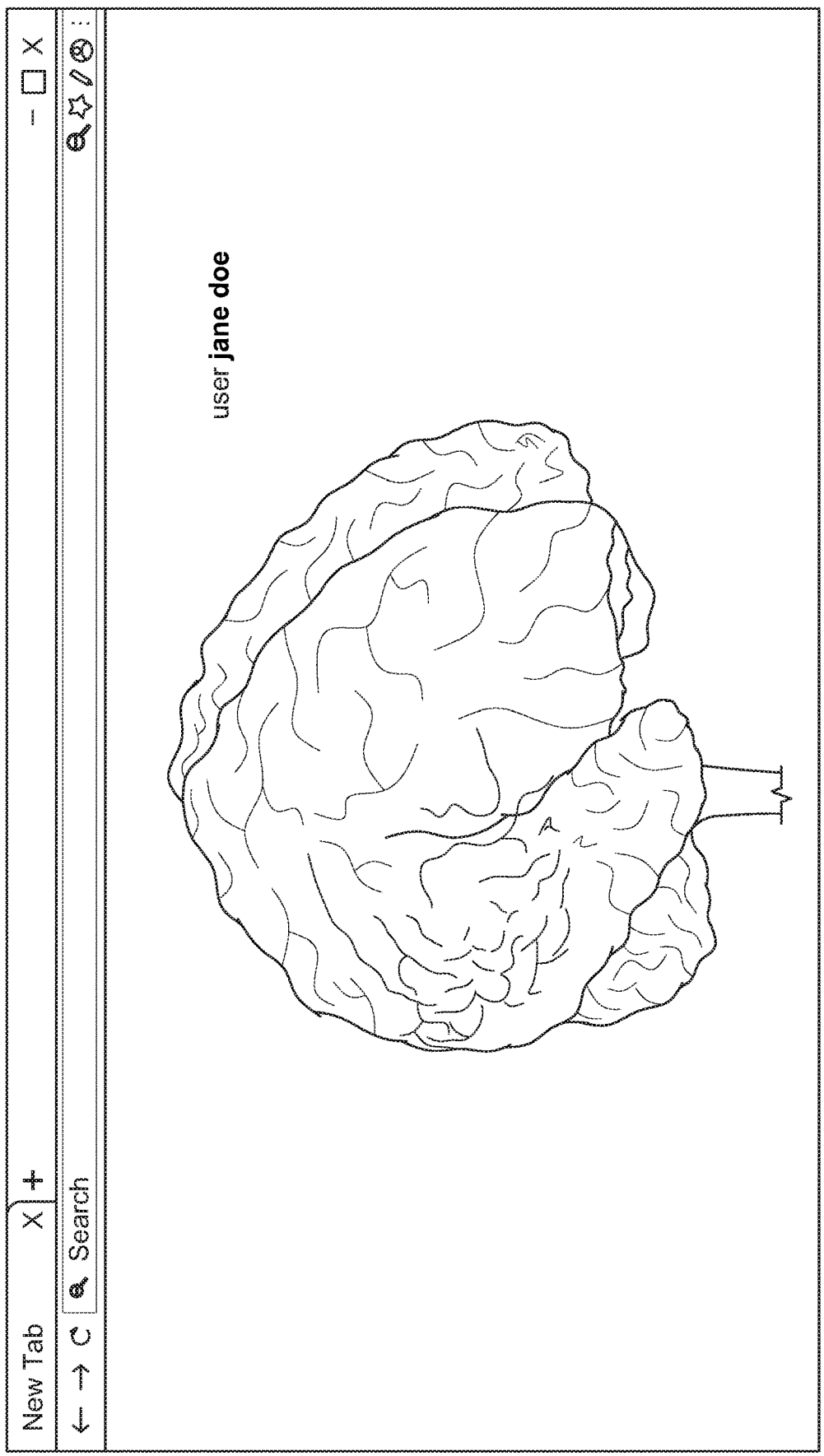
Figure 10B:
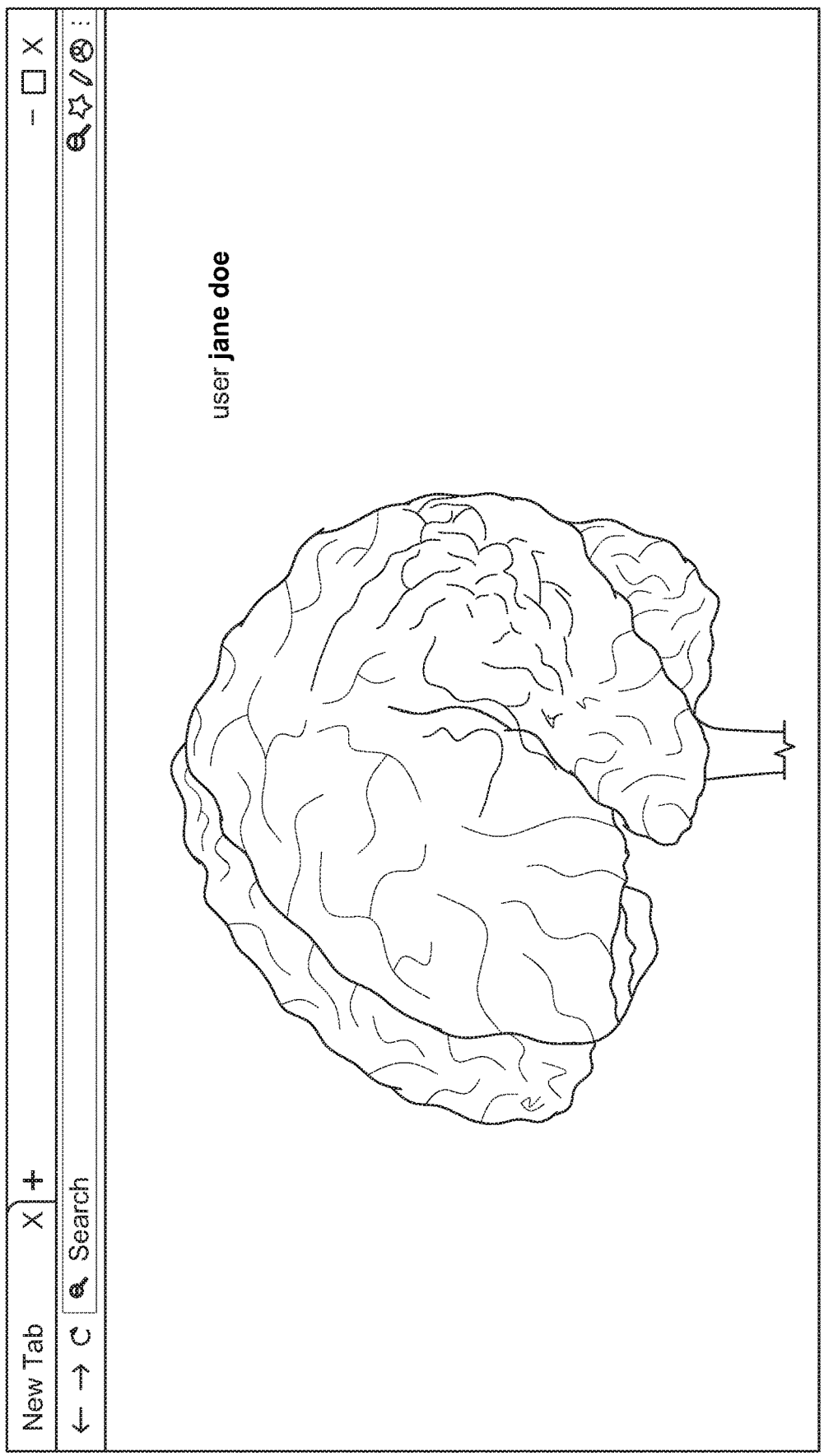
Figure 10C:
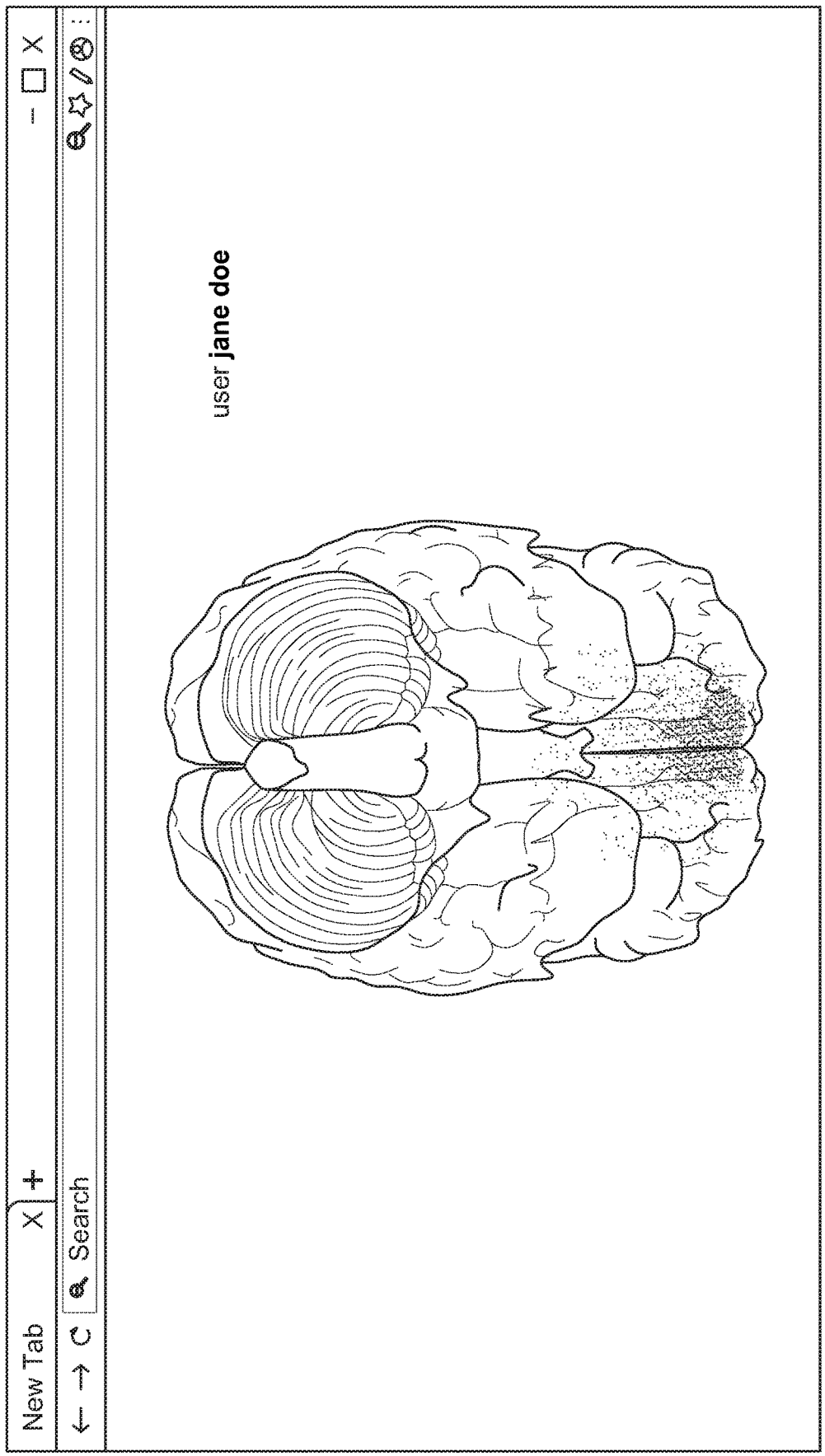
Figure 10D:
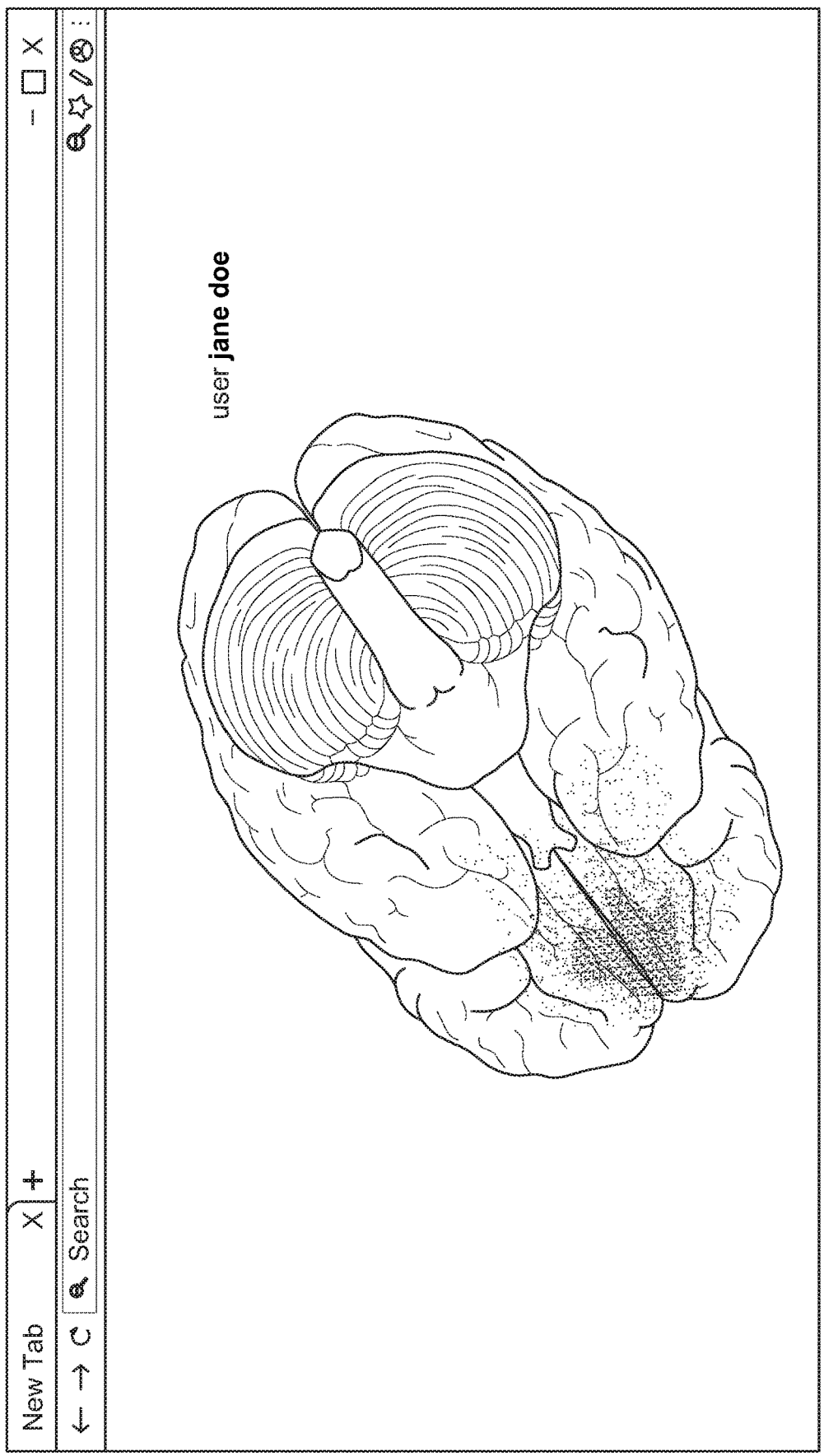
Figure 10E:
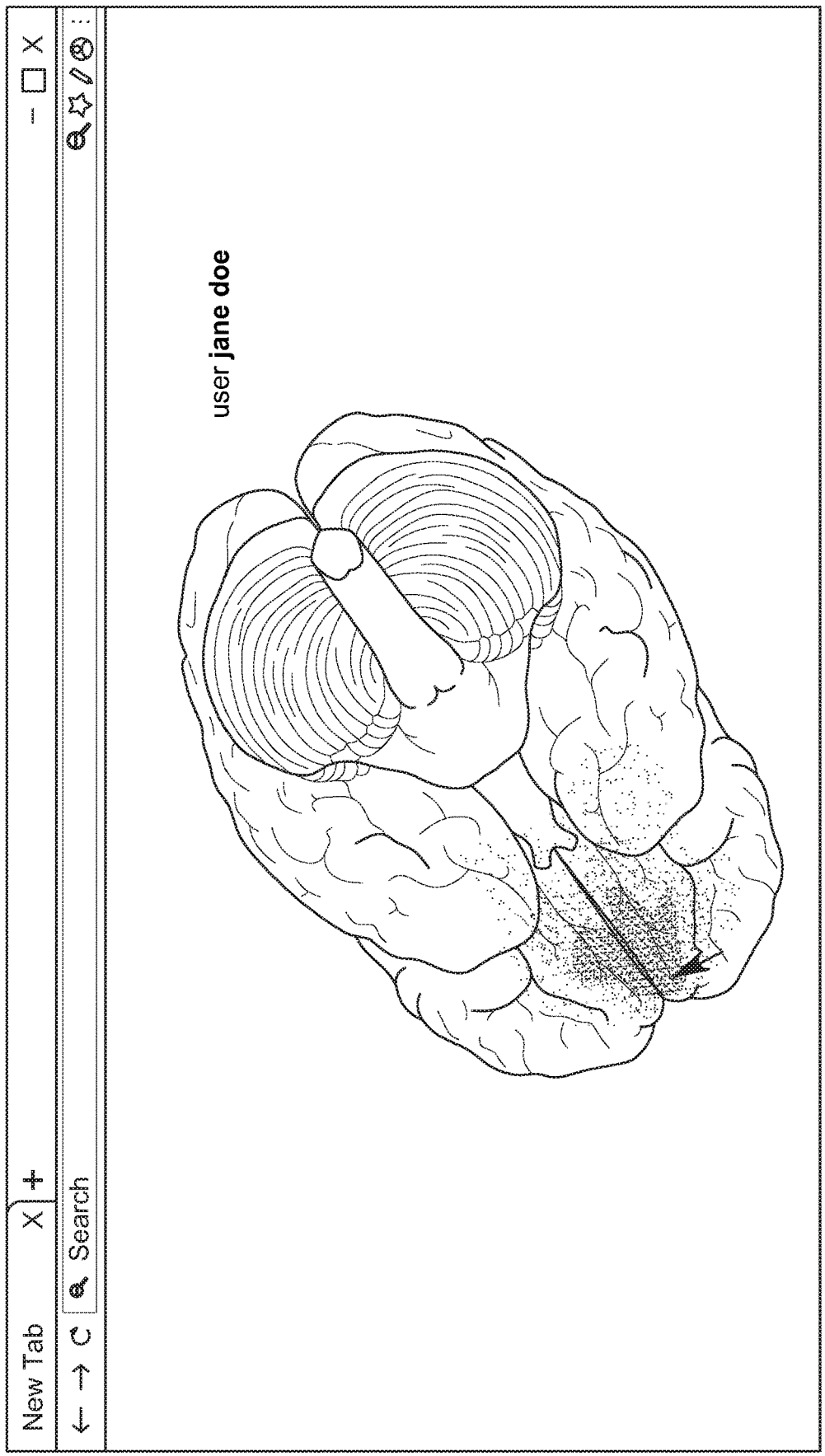
Figure 10H:
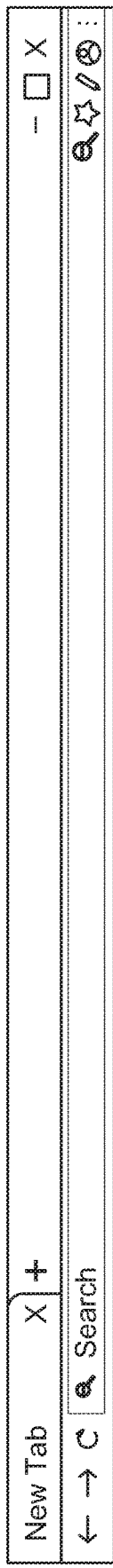

FIGS. 10A-10H illustrate user interface examples in connection with 210 in system 200 as well as user experiential process 300. In this example, the interface is implemented in an Internet browser and/or a mobile application, or other personal viewing device, though other media that may allow a user to access the interface are contemplated by the present invention. The interface provides two views to the user: a three-dimensional view and a two-dimensional view. By using a device such as a computer mouse, touch pad, or touch screen, the user can turn or rotate the brain, zoom in or out, or click on certain brain areas in order to obtain more detailed information. FIG. 10A shows an interface example for a three-dimensional view of user Jane Doe's brain after an fMRI scan. The brain image may be laid-over with functional activation as indicated by, for example, differently shaded or colored brain regions. Alternatively, the view may be of two-dimensional slices of the brain, such as coronal, sagittal, or other slices and perspectives as are known in the art. FIG. 10B shows an interface example for another three-dimensional view of user Jane Doe's brain. Compared to FIG. 10A, the brain in FIG. 10B has been turned around its vertical axis. Such movement may be accomplished by a device such as a computer mouse, touch pad, touch screen or other device that allows for manipulation of visualizations by a user. FIG. 10C shows an interface example of the inferior view of user Jane Doe's brain, though the present invention is of course not limited to such an example and other three-dimensional views as are known in the art are possible. In FIG. 10C, shading represents functional activation detected in brain regions. FIG. 10D shows an interface example of another inferior view user Jane Doe's brain, rotated about the vertical axis. FIG. 10E shows the view as FIG. 10D, but with an exemplary cursor added showing how the user can select certain brain areas, such as where activation has been detected. By selecting a brain area, the user can obtain more detailed information about that area and the user's individualized results, as shown in FIG. 10F. In this particular illustrative example, the user has selected a prefrontal area of the brain, which is associated with working memory and that has demonstrated functional activation during a task of interest, as seen by the shading. When the user clicks the brain area, the interface summarizes relevant details of user Jane Doe's activation in the selected prefrontal area of the brain. As seen in FIG. 10F, user Jane Doe's activation in this area is 75% stronger than that of her peers. The activation is shown to predict financial success to 85%, happiness to 10%, and dementia to 5%. A link is provided through which the user can obtain a list of relevant recent publications on this brain area, or any brain area the user has selected. Another link directs the user to customized recommendations for strengthening this brain area, or any brain area the user has selected. Another link provides information on how to schedule another brain scan. FIG. 10G depicts the interface a user interacts with after selecting the "these recommendations" hyperlink seen in FIG. 10F. Before receiving recommendations, the user is asked to complete an assessment of his or her personal health-risk propensity. In this example, an eight-item survey scale is used, though other surveys or assessments of personal health-risk may be used. After completing the assessment, the user learns about his/her personal health-risk propensity score in FIG. 10H.

Although the present invention has been described in some detail for purposes of clarity of understanding, it will be apparent that certain changes and modifications may be practiced within the scope of the appended claims. Therefore, the present embodiments are to be considered as illustrative and not restrictive and the invention is not limited to the details and embodiments given herein, but may be modified within the scope and equivalents of the appended claims.

What is claimed is:

1. A computer-implemented method for calculating voxel-level differences between functional and anatomical body organ images of a first user and functional and anatomical body organ images of a plurality of users, graphically visualizing said functional and anatomical body organ images of said first user in three-dimensional renderings, and computing customized functional and anatomical body organ health recommendations that afford more accurate and less time-consuming diagnoses of body organ health at an individual level along with an easy-to-navigate multi-dimensional visualization that facilitates a user's exploration of body organs, comprising:
- extracting light intensity values from each of a large multitude of small-sized voxels of each functional and anatomical image of at least one body organ of said first user and then classifying said light intensity values with:
  - behavioral information of said first user; and
  - self-reported information of said first user;
- providing at least one computer processor loaded with software configured and operable to train an artificial neural network on a large-scale database comprising previously existing information of a plurality of users, said previously existing information comprising:
  - light intensity values from each voxel of each functional and anatomical image of at least one body organ of said plurality of users classified with:
    - behavioral information of said plurality of users; and self-reported information of said plurality of users;
- determining, using said at least one computer processor, and based at least in part on said artificial neural network:
  - a predicted functional and anatomical body organ health of said first user by automatically co-registering said new information with said previously existing information;
  - and a predicted benchmark of functional and anatomical body organ health of said first user by automatically co-registering said at least one of anatomical and functional information of said first user with said previously existing information;
- storing in said database said light intensity values from each voxel of each functional and anatomical image of at least one body organ of said first user and using said updated database for retraining said artificial neural network based on said new information; and
- graphically visualizing said classified light intensity values along with markers of said predicted functional and anatomical body organ health in three-dimensional renderings;
- notifying, by computer, said first user about the functional and anatomical body organ health of said first user and providing access to said graphical visualization.

2. The computer-implemented method of claim 1, wherein said at least one body organ of said first user is a human brain.

3. The computer-implemented method of claim 1, wherein said combination of data of said plurality of users is used to train said artificial neural network to provide a highly accurate prediction of functional and anatomical body organ health of said first user.

4. The computer-implemented method of claim 1, wherein said predicted functional and anatomical body organ health and said predicted benchmark of functional and anatomical body organ health are compared against thresholds derived based on information from a plurality of users to determine abnormalities, malfunctions, deviations, and other irregularities in a prediction accuracy, a behavioral performance, or a self-reported response of said first user.

5. The computer-implemented method of claim 1, wherein said predicted functional and anatomical body organ health and said predicted benchmark of body organ health are used to make functional and anatomical body organ health recommendations via a user interface.

6. The computer-implemented method of claim 1, wherein said predicted functional and anatomical body organ health and said predicted benchmark of functional and anatomical body organ health are used to enable said first user and a specialist health practitioners to access a same information via a user interface.

7. The computer-implemented method of claim 1, wherein said predicted functional and anatomical body organ health and said predicted functional and anatomical body organ health comparisons are based on prediction accuracies.

8. The computer-implemented method of claim 1, wherein said artificial neural network is at least one of a convolutional neural network, a long short-term memory neural network, and a recurrent neural network employing a deep learning technique.

9. A computer program product for calculating voxel-level differences between functional and anatomical body organ images of a first user and functional and anatomical body organ images of a plurality of users, graphically visualizing said functional and anatomical body organ images of said first user in three-dimensional renderings, and providing customized functional and anatomical body organ health recommendations comprising at least one machine-readable medium, said at least one machine-readable medium storing instructions, the instructions comprising:
- instructions which when executed by at least one processor cause extracting light intensity values from each of a large multitude of small-sized voxels of each functional and anatomical image of at least one body organ of said first user and then classifying said light intensity values with:
  - behavioral information of said first user; and
  - self-reported information of said first user;
- instructions which when executed by at least one processor cause providing at least one computer processor loaded with software configured and operable to train an artificial neural network on a large-scale database comprising previously existing information of a plurality of users, said previously existing information comprising:
  - light intensity values from each voxel of each functional and anatomical image of at least one body organ of said plurality of users classified with:
    - behavioral information of said plurality of users;
    - and self-reported information of said plurality of users;
- instructions which when executed by at least one processor cause determining, using said at least one computer processor, and based at least in part on said artificial neural network:
  - a predicted functional and anatomical body organ health of said first user by automatically co-registering said new information with said previously existing information;
  - and a predicted benchmark of functional and anatomical body organ health of said first user by automatically co-registering said at least one of anatomical and functional information of said first user with said previously existing information;

instructions which when executed by at least one processor cause storing in said database the said light intensity values of said first user and determined classes of each functional and anatomical image and using said updated database for retraining said artificial neural network based on said new information; and graphically visualizing said classified light intensity values along with markers of said predicted functional and anatomical body organ health in three-dimensional renderings;

instructions which when executed by at least one processor cause notifying, by computer, said first user about the functional and anatomical body organ health of said first user along with access to said graphical visualization.

10. The computer program product of claim 9, wherein said computer program product is a multi-dimensional visualization and functional and anatomical body organ health recommendation system, which is configured to be accessed via a graphical user interface for displaying visualizations of said first user's body organ; prediction and comparison reports; suggestions on scholarly publications relevant to certain body organs; referrals to specialists that are directed toward certain aspects of said first user's body organ and/or body organ function; opportunities for information sharing with other people; and personalized body organ health recommendations.

11. The computer program product of claim 9, wherein said artificial neural network is at least one of a convolutional neural network, a long short-term memory neural network, and a recurrent neural network configured to employ a deep learning technique.

* * * * *